United States Patent
Parselle et al.

(10) Patent No.: US 9,011,657 B2
(45) Date of Patent: Apr. 21, 2015

(54) COMBINATION OF BREATHALYSER AND ELECTROCHEMICAL SALIVA DRUG TEST

(75) Inventors: John Parselle, Sussex (GB); Craig Banks, Cheshire (GB); Peter Leslie James McMillan, Wollstonecraft (AU); Angelo Kotsis, Marrickville (AU)

(73) Assignee: Oxtox Limited, Oxford (GB)

( * ) Notice: Subject to any disclaimer, the term of this patent is extended or adjusted under 35 U.S.C. 154(b) by 716 days.

(21) Appl. No.: 13/375,991

(22) PCT Filed: Jun. 4, 2010

(86) PCT No.: PCT/GB2010/001095
§ 371 (c)(1),
(2), (4) Date: Feb. 21, 2012

(87) PCT Pub. No.: WO2010/139955
PCT Pub. Date: Dec. 9, 2010

(65) Prior Publication Data
US 2012/0132524 A1 May 31, 2012

(30) Foreign Application Priority Data
Jun. 4, 2009 (GB) .................................. 0909608.2

(51) Int. Cl.
*G01N 27/327* (2006.01)
*A61B 5/08* (2006.01)
*G01N 33/487* (2006.01)
*G01N 33/497* (2006.01)

(52) U.S. Cl.
CPC ...... *G01N 33/48714* (2013.01); *G01N 33/4972* (2013.01)

(58) Field of Classification Search
USPC ............... 204/403.01–403.15, 416–418, 424; 600/532
See application file for complete search history.

(56) References Cited

U.S. PATENT DOCUMENTS

| | | | |
|---|---|---|---|
| 5,260,031 A | 11/1993 | Seymour | |
| 5,656,142 A * | 8/1997 | Park et al. | 204/403.1 |
| 6,061,586 A | 5/2000 | Kuperman et al. | |
| 2001/0023324 A1* | 9/2001 | Pronovost et al. | 600/582 |
| 2003/0121779 A1 | 7/2003 | Kidwell | |
| 2007/0015286 A1 | 1/2007 | Neel et al. | |
| 2009/0054799 A1* | 2/2009 | Vrtis et al. | 600/532 |

FOREIGN PATENT DOCUMENTS

| | | |
|---|---|---|
| EP | 0866966 B1 | 9/2001 |
| JP | 2003-294679 A * | 10/2003 ................ 27/327 |

OTHER PUBLICATIONS

Derwent English language Abstract of Ogasa JP 2003-294679 A, patent published Oct. 15, 2003.*
JPO computer-generated English language translation of Ogasa JP 2003-294679 A, patent published Oct. 15, 2003.*
U.S. Appl. No. 61/001,172, field Oct. 31, 2007.*
International Search Report for PCT/GB2010/001095 dated Sep. 9, 2010.

* cited by examiner

*Primary Examiner* — Alex Noguerola
(74) *Attorney, Agent, or Firm* — Banner & Witcoff, Ltd.

(57) ABSTRACT

A device combining a fuel-cell-type breathalyzer with an electrochemical saliva drug test. The saliva drug tester comprises a disposable test strip-electrode module assembly and an analyzer module. The saliva is squeezed out of an absorbent swab when the test strip is inserted into the electrode module. The electrode module can also carry information that is read and evaluated by the analyzer, e.g. for verification of the electrode module.

37 Claims, 5 Drawing Sheets

COMBINATION OF BREATHALYSER AND ELECTROCHEMICAL SALIVA DRUG TEST

CROSS REFERENCE TO RELATED APPLICATIONS

This application is a National Stage application of co-pending PCT application PCT/GB2010/001095 filed Jun. 4, 2010, which claims the benefit of GB application number 0909608.2 filed Jun. 4, 2009. These applications are incorporated herein by reference in their entireties.

This invention relates to electrochemical assays for determining the presence or quantity of analyte in a fluid sample, e.g. a human bodily fluid such as breath or saliva, and to equipment for performing such assays.

A wide variety of assays performed on samples of human bodily fluids are known in the art. Conventionally fluid samples would need to be taken by a physician or other medical personnel and sent away to a laboratory for performance of the appropriate assay and analysis of the results. More recently, however, there has been a growth in the availability of assays which can be carried out in real time close to the subject from which the sample is obtained, i.e. without the need to send samples away for laboratory analysis. A good example of this is the measuring of glucose levels in blood using handheld electrochemical assay devices which can be operated by a person suffering from diabetes in order to allow them to measure their instantaneous blood glucose level to assist in the management of their condition.

The applicant has also appreciated that there are many other useful assays which can be carried out on other body fluids.

When viewed from a first aspect the present invention provides a device for performing at least two assays on separate body fluids comprising means for carrying out a first electrochemical assay for a first analyte in a sample of breath and means for carrying out a second electrochemical assay for a second analyte in a sample of liquid.

Thus it will be seen that in accordance with the invention a single device can be used to carry out separate assays. The invention may be used with a wide variety of different electrochemical assays on a number of different types of fluids.

In the case of both the first and second assays, each could be a simple presence or threshold assay but it is preferred for each that it is quantitative assay.

In a set of preferred embodiments the first analyte is ethanol—i.e. the device can be used as a 'breathalyser' of the type typically used to determine whether an individual has consumed an excessive amount of alcohol for a given activity such as driving. Any suitable assay could be used. Preferably the assay comprises a standard fuel cell ethanol assay.

The second assay can advantageously be used to test for another analyte of relevance when testing for alcohol. In a set of preferred embodiments, the second assay is adapted for use with human saliva samples, and thus the invention is considered to extend to the use of apparatus or systems in accordance with any aspect of the invention for the electrochemical assaying of human saliva samples.

In one set of preferred embodiments, the second assay means electrodes are adapted to detect one of more of: phenols, phenolic compounds and phenol derivatives such as tetrahydracannabinol as is described in greater detail in WO 2006/134386 in order to allow the system to be used for testing for the use of cannabis by the subject.

Thus in an advantageous set of embodiments the device can be used to test both for impairment through alcohol and through use of other drugs. This makes it particularly convenient for use by the police and other law enforcement agencies, or for use in other circumstances where it is desirable to be able to test for impairment.

The degree of integration between the two assays is not essential. Thus in some embodiments they could be entirely independent of one another except for being housed in the same device. In a set preferred embodiments the first and second assays use a common power supply such as a battery and/or a common user control interface and/or a common display.

The second assay preferably comprises a swab having an absorbent portion for receiving and retaining a fluid sample, an electrode module comprising at least one electrode, said electrode module being arranged such that it can be selectively placed over said absorbent portion in order to contact said electrode with said fluid sample, the device comprising a reader module configured to process signals from said electrode module.

This is novel and inventive in its own right and thus when viewed from a further aspect the invention provides a device for performing at least two assays on separate body fluids comprising means for carrying out a first electrochemical assay for a first analyte in a sample of breath and means for carrying out a second electrochemical assay for a second analyte in a sample of liquid wherein the means for carrying out the second assay comprises a swab having an absorbent portion for receiving and retaining a fluid sample, an electrode module comprising at least one electrode, said electrode module being arranged such that it can be selectively placed over said absorbent portion in order to contact said electrode with said fluid sample, the device comprising a reader module configured to process signals from said electrode module.

Preferably said electrode module and said reader module are arranged such that they can be coupled together for communication of said signals from said electrode module to said reader module.

Thus it will be seen by those skilled in the art that in accordance with the preferred embodiments of the invention to carry out the second assay a sample can be collected on a swab and analysed by electrodes in an electrode module in combination with a reader module. Whilst it is envisaged that there may be circumstances where the whole apparatus is designed to be single-use or where it might be appropriate to re-use a particular set of electrodes, preferably the electrode module is removable from the reader module such that it can be cleaned, or more preferably, disposed of. This is clearly advantageous from the point of view of avoiding cross-contamination and also, more generally, from the ability to increase the level of hygiene associated with use of the device. Thus, in such an embodiment it is envisaged that the swab and electrode module will both be designed to be used only once and then discarded.

Preferably the electrode module and swab are designed for single use.

In one set of preferred embodiments, the electrode module can be locked in place over the absorbent portion of the swab member. This has several advantages. Firstly, it can help to ensure that there is proper registration between the absorbent portion and the electrode module. Secondly, it prevents unauthorised re-use of a swab or electrode module, thereby avoiding the risk of cross-contamination. Thirdly, it enables hygienic disposal of the swab and electrode module by preventing inadvertent access to the fluid on the absorbent portion of the swab and/or the electrode module.

In accordance with all aspects of the invention, there are many different ways in which the swab and electrode module can be configured in order to give the described functionality.

For example, there are a variety of possible mechanisms for bringing the electrode module into position over the absorbent portion of the swab. In one set of possible embodiments, the electrode module is, or is able to be, rotatably fitted to the swab so as to have an open configuration allowing access to the absorbent portion in order to collect a fluid sample; and a closed configuration in which the absorbent portion is inside the electrode module so that the electrodes thereof can come into contact with the fluid sample. The electrode module might be provided permanently on the swab or it might be provided separately and able to be manually clipped or otherwise attached to it.

In another set of embodiments, the electrode module can be slid over the absorbent portion of the swab member. Again, the electrode module could be permanently fitted to the swab and thus able to slide along it or, as presently preferred, the electrode module might fit over the absorbent portion, e.g. in the manner of a cap or sleeve fitted to an end of the swab member.

It is envisaged that the electrode module will contain all of the electrodes needed to carry out the second assay. Typically this would comprise a working electrode, a counter electrode and a reference electrode (although such a configuration is not considered essential). However in an alternative possibility one or more of the electrodes could be provided on the swab itself—e.g. in such a position that the electrode is placed in contact with the fluid sample when the sample is received.

In accordance with preferred embodiments of the invention, an electrode module is placed over an absorbent portion of a swab so that one or more electrodes thereof are brought into contact with the fluid sample retained in the absorbent portion. Either or both of the electrode module and the swab is preferably configured to apply a contact pressure between said electrodes and the fluid sample retained in the absorbent portion. The Applicant has found that this increases the reliability of the electrochemical assay being carried out.

There are of course many possible mechanisms for doing this. For example, one or both elements may comprise resilient means to provide the desired contact pressure. Alternatively, the pressure could be provided by the action of sliding, rotating or otherwise moving the electrode module over the absorbent portion. One illustrative example of this might be mutually acting cam means.

In other embodiments of the features set out above, the pressure could be applied independently of the action of bringing the electrode module and absorbent portion into registration. For example, the pressure could be applied completely manually, perhaps by means of a suitable button or lever. Alternatively, a latch or detent might be manually released in order to apply said pressure with a pre-tensioned resilient arrangement. In one set of particularly convenient embodiments, the aforementioned contact pressure is provided by the action of locking the electrode module to the swab. The advantages of this latter feature have been set out hereinabove. It is further envisaged that this action could be coupled in turn to the action of bringing the electrode module into registration with the absorbent portion of the swab. The convenience of such an embodiment is clear—namely that simply by placing the electrode module onto the appropriate part of the swab, the appropriate contact pressure can be automatically applied and the electrode module locked in such a position at the same time.

Although in the embodiments depicted herein the swab is embodied as an elongate member with the absorbent portion at one end, i.e. in a similar configuration to a traditional swab, the invention is not limited to such arrangements and no specific features or limitations should be inferred from the use of the term "swab". For example, the swab might be designed to be fitted to another member, tool, device or machine prior to use or prior to bringing the absorbent portion thereof into registration with the electrode module. To take an example, arrangements are envisaged whereby a reusable tool or device has a disposable swab part fitted thereto.

Moreover the reference to an absorbent portion of the swab should not be understood as excluding the possibility of the entire swab being absorbent or of the same material. For example, the fluid sample might be received by just part or indeed all of an absorbent article comprising the swab. In other words, the absorbent portion could constitute the whole of the swab. One example of this might be an absorbent pad which is taken into the mouth of a user to absorb saliva and then placed into an apparatus such that it is brought into contact with the electrode of an electrode module.

The above notwithstanding, some of the embodiments of the invention comprise an elongate swab with the absorbent portion at one end and a handling portion at the other end. In preferred examples of such embodiments, the swab is provided with means disposed between the absorbent portion and the handling portion to inhibit fluid running down the swab from the absorbent portion to the handling portion. Such means could comprise a recess, but preferably comprises a protruding barrier.

In aspects of the invention in which an electrode module can be coupled to a reader module in order to transfer signals from one to the other, it is envisaged that a wireless coupling could be provided e.g. with the signals encoded on a radio, infrared or ultrasonic transmission. More preferably however a wired connection is provided for reasons of cost effectiveness. The electrode module could comprise means for performing some processing or filtering of the signals from the electrodes. In preferred embodiments, however, the electrode module simply permits a direct connection to the electrodes, with any such filtering and processing being carried out in the reader module. This is clearly consistent with making the electrode module disposable and producible at a minimum cost and therefore disposable.

Preferably the coupling between the electrode module and the reader module comprises a simple plug-and-socket arrangement. In preferred embodiments the reader module is configured to indicate whether the electrode module has been properly connected to it. In some embodiments the reader module may be configured to identify or verify the electrode module. There might be several reasons for doing this. It could, for example, be used to ensure that the electrode module is from an authorised source, or that it is within an authorised shelf life. Another possibility which is given by having a separate reader module and electrode module is that different assay modules could be used with a common reader module. For example the first essay could be performed using a disposable module connected to the reader module.

In such arrangements the reader module might then be configured to determine automatically what type of module had been connected to it and to perform the appropriate analysis as a consequence.

The electrode module could be provided with the minimum set of electrodes to perform the second assay. As previously mentioned this typically consists of a working electrode, a counter electrode and reference electrode, although this is not essential. However in accordance with some embodiments, one or more additional working electrodes is provided.

In one set of embodiments the plurality of working electrodes are configured to detect two or more analytes. For example each working electrode could be configured to detect a different analyte. The applicant has appreciated that in the context of a real time, on-the-spot assay it is advantageous to be able to test for more than one analyte simultaneously, as opposed to having to carry out a series of tests, especially if each requires a fresh sample. As mentioned previously one potentially useful application of the invention would be a roadside driver impairment test where various substances known to cause impairment of driving function could be tested for, such as cannabis, cocaine, heroin etc in addition to an alcohol breath test. In one possible embodiment, the electrode module of the second assay is adapted to detect cannabis and amphetamines simultaneously. In other particular embodiments it could be adapted to detect any or all substances from the group comprising cannabis, amphetamines, cocaine, opiates and benzodiazepines. Of course the skilled person will appreciate that any number and combination of substances can be tested for.

In another set of embodiments a plurality of working electrodes, conveniently identical to one another, is provided for a single given analyte. It effectively allows multiple parallel second assays to be carried out simultaneously on the same liquid sample which can be exploited by the use of appropriate statistical techniques to give an accurate result. Also in some instances it can reduce the volume of liquid required to give a reliable measurement. These are both important factors in the applications envisaged for this technology. Of course an electrode module embodying this feature could still carry respective sets electrodes for a plurality of analytes; each set may comprise one or more working electrodes.

The working electrodes could each form part of an independent set of electrodes for performing the second assay—e.g. each working electrode could have its own associated reference and counter electrodes. Preferably however two or more working electrodes share a common reference or counter electrode.

In one set of preferred embodiments a plurality of working electrodes is arranged around a common reference or counter electrode, e.g. in a circle. This provides a compact arrangement of the electrodes in the electrode module on which it is convenient, in preferred embodiments for a swab carrying the sample to be placed The number of working electrodes may be selected as appropriate for the application. To give some non-limiting examples there may be between 2 and 30 working electrodes, or between 5 and 20 or between 8 and 16. In one specific example there are 12.

Preferably the working electrodes are each less than 2 mm wide, more preferably less than 1 mm wide. Small working electrodes allow a large number working electrodes to be fitted into a small area, either as part of an electrode array or an electrode module, while still remaining independent. This is advantageous because the swab does not therefore have to be unduly large to provide a sample across the whole area of the working electrodes which will be able to return an accurate measurement with only a small sample. It also enables a highly accurate measurement to be made as a result of the large number of working electrodes.

The working electrodes could be connected together on the electrode module so as to act effectively as a single distributed electrode. Preferably however the plurality of working electrodes have individual contacts to allow electrical connection to be made to them individually. This allows the working electrodes to be addressed individually which enhances the accuracy of the measurement by allowing multiple independent measurements be made, therefore decreasing the statistical error on the measurement.

Preferably the reader module adapted to be used in association with the embodiments of the electrode module described above is configured to address the working electrodes in parallel. Addressing the electrodes in parallel allows the measurements at the electrodes to be made simultaneously which increases the speed with which the measurement can be taken. This is clearly advantageous when an instantaneous measurement is desired.

Preferably the contacts for the electrodes are provided along one edge of the electrode module. Contacts passing to the edge of the electrode module allow an easy push-in connection to be made with a, or the, reader module.

A preferred embodiment of the invention will now be described, by way of example only, with reference to the accompanying drawings in which:

FIG. 2b is a cross-sectional view on line A-A of FIG. 2a;

FIG. 2c is a cross-sectional view on line B-B of FIG. 2a;

Figure 1:
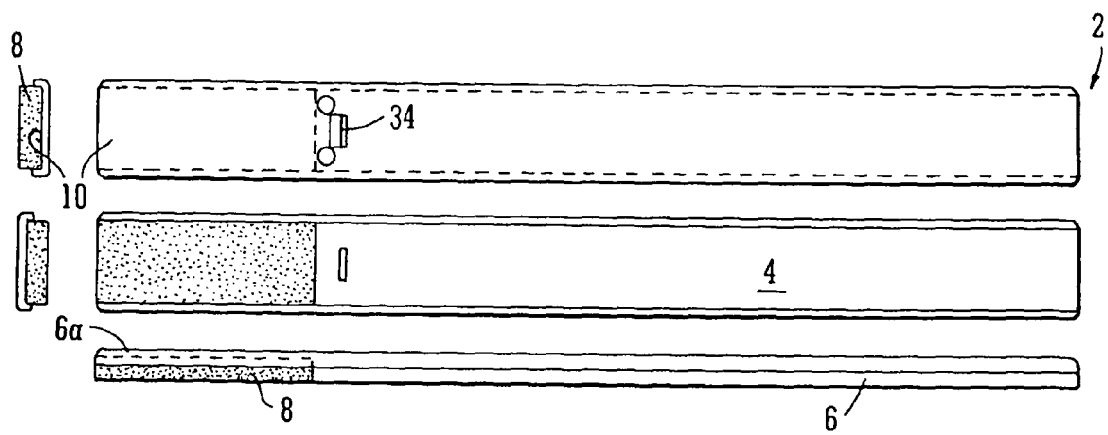
FIG. 1 shows various elevations of a swab for use with embodiments of the invention.

FIG. 1 shows various elevations of a swab 2 for use in respect of a second assay with a device embodying the invention. The swab comprises an elongate rectangular body section 4 which has two longitudinal vertically protruding walls along its respective outer edges. At the left-hand edge of the swab (as viewed from FIG. 1) there is a rectangular absorbent foam pad 8 attached to the upper face of the swab. A recess 10 is formed on the upper face of the body 4 in order to accommodate the absorbent pad 8. This can be seen from the end elevations to the left of FIG. 1. It will also be noted from the side elevation that the lateral walls of the swab 6a drop down adjacent the absorbent pad 8. Longitudinally behind the pad recess 10 is a recess 34, the purpose of which will become apparent later.

Figure 2A:
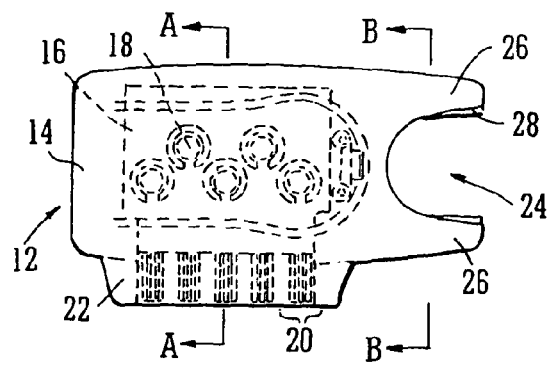
FIG. 2a is a partially transparent view of an electrode module for use with embodiments of the invention.
Figure 2B:
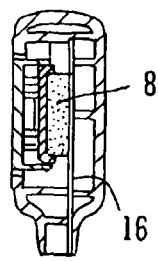
Figure 2C:
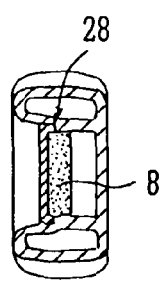

FIGS. 2a to 2c show the electrode module 12. In FIG. 2a the body 14 of the module is shown partly transparent in order to allow the inner structure thereof to be seen. Inside the main part of the module is an electrode assembly 16 comprising five independent electrode arrangements 18 (described in greater detail below with reference to FIG. 4). Each of the electrode arrangements 18 is connected to a respective set of three contact strips 20 which extend into a lateral extension of the electrode module body to form a plug portion 22.

At the right-hand end (as viewed from FIG. 2a) of the module 12 is a mouth portion 24 flanked by two lateral jaws 26 which define respective ledges 28 on their inner inwardly facing edges on which the edge of the swab 6a adjacent the absorbent pad 8 can slide (see FIG. 2c).

FIG. 2c is a section on line B-B showing the swab of FIG. 1 partially inserted into the electrode module 12. As the front end, of the swab 2 is inserted into the mouth portion 24 of the module, the side walls 6a adjacent the absorbent pad 8 slide along the ledges 28 in order to keep the pad 8 clear of the edges of body 24a when the end of the swab is inserted into a longitudinal channel therein.

Referring now to FIG. 2b, it can be seen that when the swab is inserted further into the electrode module, the absorbent pad wipes over the electrode assembly 16. The pad 8 is pressed against the electrode module 16 by a hinged plate 30 which is described in more detail below with reference to FIGS. 3a to 3d.

Figure 3A:
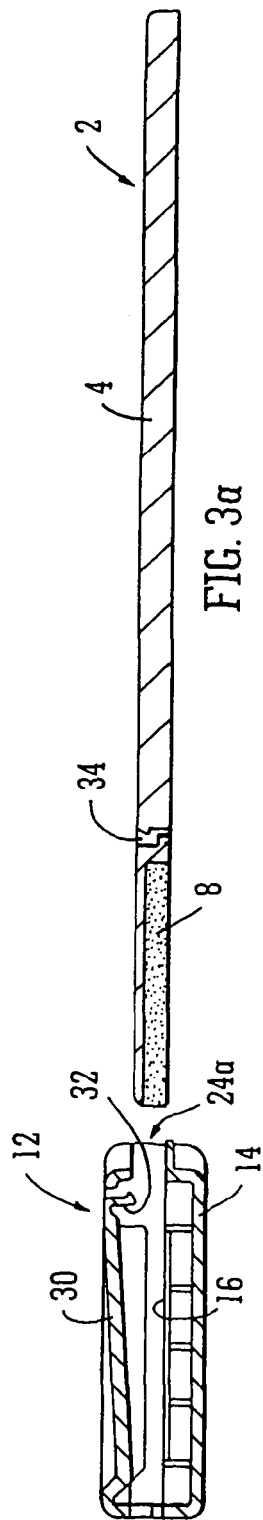
FIGS. 3a to 3d are respective cross-sectional views showing the swab of FIG. 1 being inserted into the electrode module.
Figure 3B:
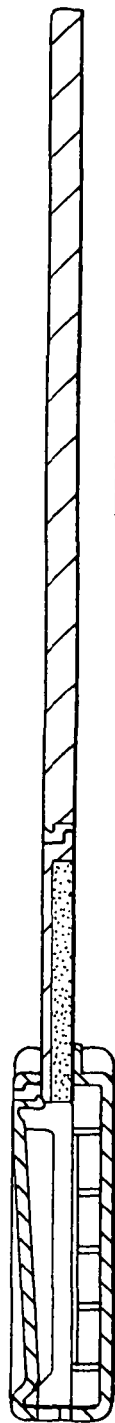
Figure 3C:
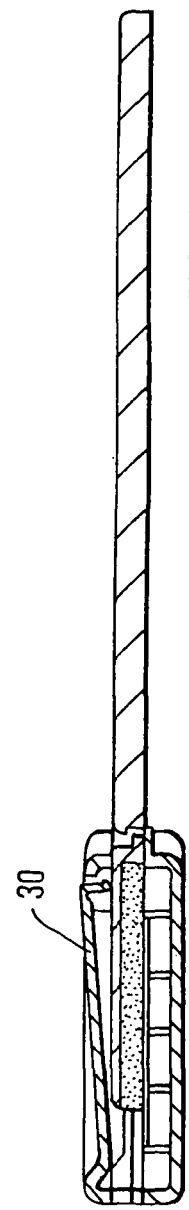
Figure 3D:
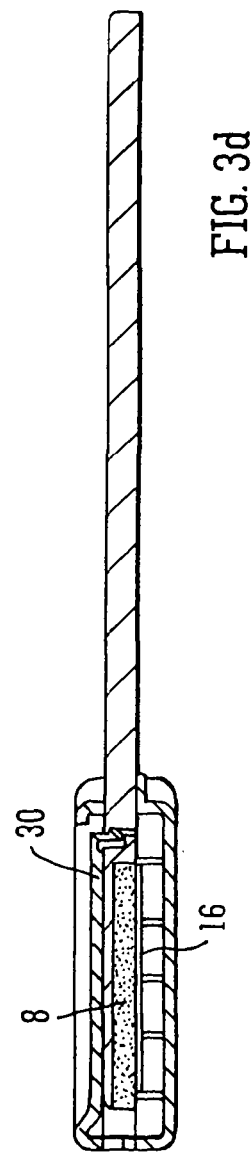

FIGS. 3a to 3d show more clearly the stages in inserting the swab 2 into the electrode module 12. Thus initially, in this embodiment at least, the electrode module 12 is separate from the swab 2 and the swab 2 is inserted into the entrance 24a to the channel defined inside the module body 14. With reference to FIG. 3b, as the end of the swab 2 is inserted further into the electrode module 12 it slightly forces up a plate 30, hinged by a moulded hinge to the module body 14 defined, by means of a downwardly extending catch feature 32 at the distal edge thereof—in a cam-like manner.

As the swab 2 is inserted fully into the electrode module 12 (FIG. 3d) the catch feature 32 of the hinged plate 30 comes into alignment with a corresponding recess feature 34 defined in the body of the swab 4. This allows a user to squeeze the upper and lower faces of the electrode module 12 together which causes the hook feature 32 to pass into the corresponding recess 34 and lock in place against the undercut portion thereof. This maintains the contact pressure between the absorbent pad 8 and the electrode assembly 16 which has been found to give a more accurate and reliable measurement. Moreover, it also means that neither the electrode module 12 nor the swab 2 can be re-used, thereby avoiding the risk of cross-contamination and/or inaccurate results. It also means that when the assembly is discarded, no casual contact with the fluid sample retained in the absorbent pad 8 is possible, thereby allowing safe and hygienic disposal.

Figure 4A:
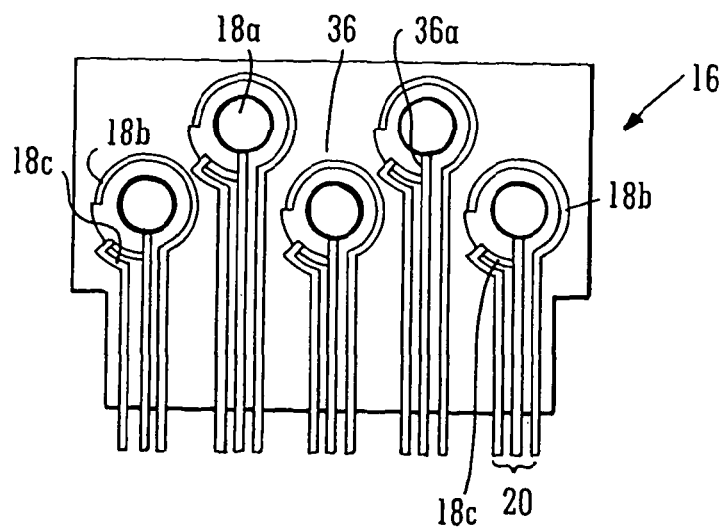
FIG. 4a is a detailed view of an electrode assembly disposed within the electrode module.

FIG. 4a is a close-up view of the electrode assembly 16 comprising five independent electrode sets 18. Each electrode set 18 comprises a working electrode 18a having a diameter of approximately 3 mm, a counter electrode 18b and a reference electrode 18c. These each have conductive tracks to take them to respective terminals 20 to allow electrical connection thereto in the reader. The working electrode 18a contains the appropriate chemical for detecting the substance of interest and varies between the five electrodes. For example it might include one of the chemicals disclosed in WO 2006/134386.

Figure 4B:
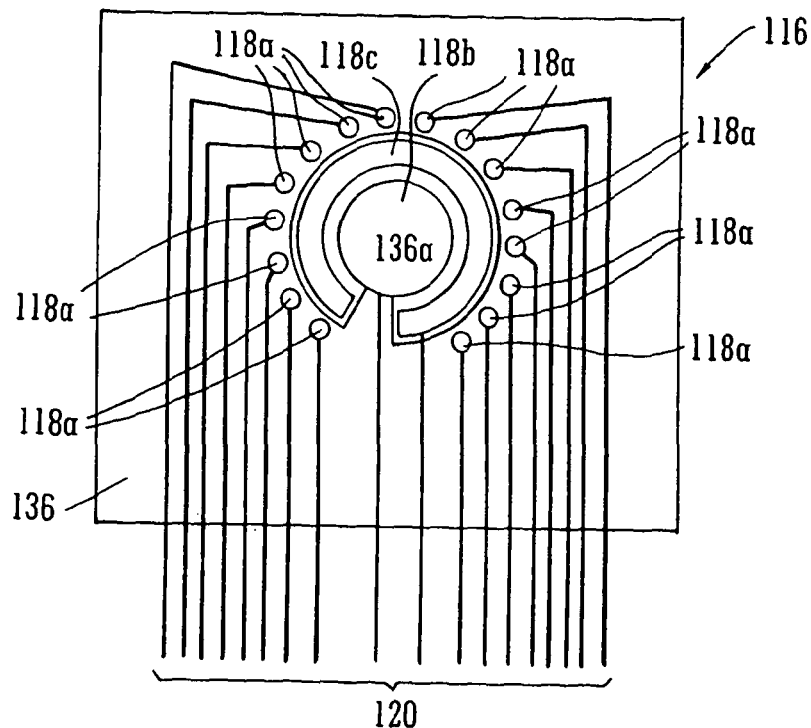
FIG. 4b is a detailed view of another electrode assembly.

FIG. 4b is a close-up schematic view of an alternative electrode assembly 116 with a single electrode set 118 comprising fourteen working electrodes 118a which share a counter electrode 118b and a reference electrode 118c. In this embodiment the reference electrode 118c is shown as arcuate segment extending round the counter electrode 118b. However in alternative embodiments the reference electrode is of similar size to the working electrodes. Also in this embodiment the working electrodes are only of the order of 1 mm in diameter which allows all fourteen working electrodes 118a to be fitted compactly around the periphery of the reference and counter electrodes 118b, 118c.

The electrodes 118a, 118b, 118c each have individual conductive tracks to take them to respective terminals 120 to allow electrical connection with the reader. Since all the contacts are brought out to a common edge of the module, a convenient push-in connection between the electrode module and the reader can be used.

The working electrodes 118a all contain same chemical for detecting the substance of interest. Again this could be one of the chemicals disclosed in WO 2006/134386. As they have their own conductive tracks and terminals 120 the working electrodes 118a can be addressed individually and in parallel, allowing multiple simultaneous measurements to be made in use. This gives a very high measurement accuracy. A simple average of the measurements could be used, although more sophisticated techniques could be used, e.g. to exclude values much lower than the rest which might arise form a particular working electrode not being properly covered with the analyte fluid.

The electrode assemblies 16, 116 can be produced in the same way. Production begins with an electrically insulating substrate made of polypropylene, but any other suitable material could be used. On top of this is laid a layer of carbon, e.g. using screen printing as is well known in the art, which forms the basis of the three electrodes 18a, 118a; 18b, 118b; 18c, 118c of each electrode set 18, 118 and also the conductive tracks to the terminals 20, 120. A layer of silver chloride ink is then added to form the reference electrode 18c, 118c.

Thereafter an insulating dielectric layer 36, 136 is printed which covers most of the area of the assembly 16, 116 except for circle apertures over the area around the electrodes 18a, 118a; 18b, 118b; 18c, 118c although there is a tab 36a, 136a which extends along the conductive track for each reference 18c, 118c.

Figure 5A:
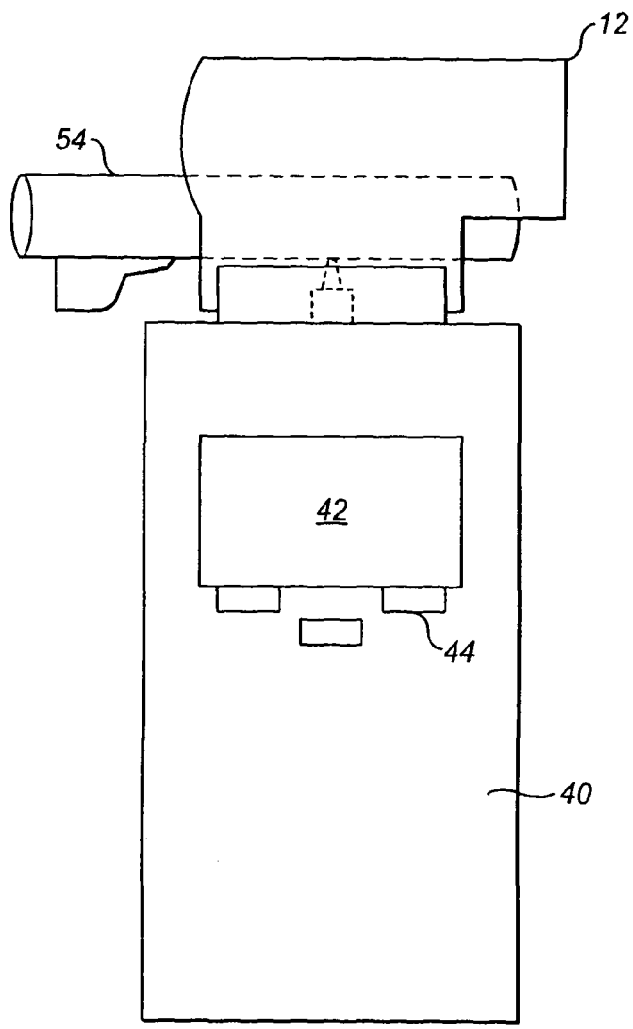
FIGS. 5a and 5b show schematically a device embodying the invention.
Figure 5B:
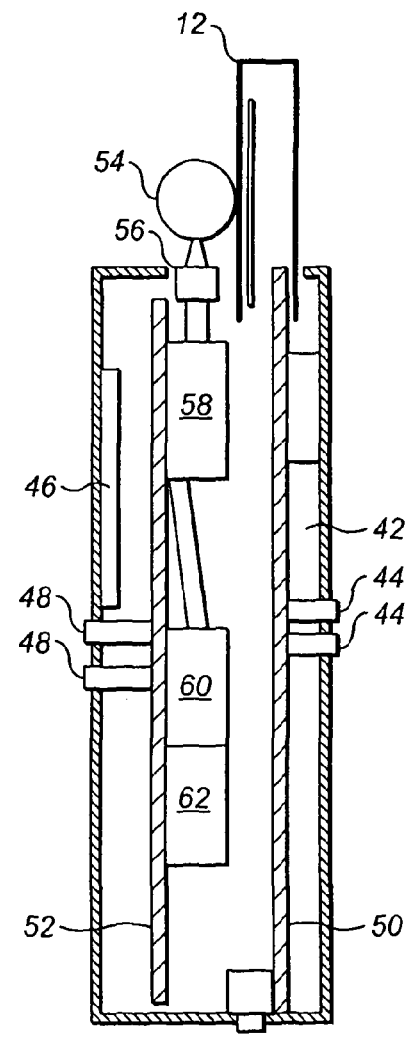

Finally the appropriate reagents are placed on the working electrodes 18a, 118a. FIGS. 5a and 5b show a device in accordance with the invention in front elevation and side cross-section respectively. The device can be used to perform both alcohol breath tests and drugs tests. It has an outer casing 40 with separate user interfaces for the respective tests on each face. On the face visible in FIG. 5a the user interface comprises a liquid crystal display (LCD) 42 and some buttons 44 for operating the drugs tester in a manner similar to that previously described. On the other face of the device are corresponding LCD 46 and buttons 48 for operating the breathalyser. The two sets of displays and controls 42, 44, 46, 48 are connected to respective printed circuit boards (PCBs) 50, 52. Although not shown a common battery can be used to power the two PCBs.

At the top of the device is an electrode module 12 as previously described which fits over an exposed edge of the PCB for the drugs tester through an aperture at the top of the housing 40. The device shown therefore acts as a reader module which allows a variety of different assays to be performed on saliva samples by inserting a suitable swab (not shown) into the electrode module in exactly the same manner as described previously. Although not shown, in practice the electrode module 12 would normally be stored in a sealed packet which might, if required, be sterile.

Once the electrode module 12 has been inserted into the device, the sample can be collected by taking a swab (not shown), again from sealed and possibly sterile packaging, and a fluid sample, e.g. saliva/oral fluid, collected from a subject, onto the absorbent portion at one end. This absorbent portion is then inserted into the electrode module 12 in a manner similar to that previously described in greater detail with reference to FIGS. 3a to 3d.

With the swab fully inserted into the electrode module 12, the electrochemical assay can be carried out, with signals from the electrodes (not shown) being passed down to the PCB 50 through the plug-and-socket connection previously described. These signals can then be analysed and the results displayed on the display screen 42. In the case of an electrode module having multiple working electrodes as shown for example in FIG. 4b, multiple measurements can be carried out simultaneously and the results combined statistically to produce a highly accurate aggregate result.

Once the assay has been satisfactorily completed, the electrode module 12 can simply be removed from the socket in the top of the device, with the swab still locked inside it, and the two parts can then be safely and hygienically disposed of.

Also at the top of the device is a breath tube 54 communicating with a radial nozzle 56 which in turn is connected to a fuel cell 58, pump 60 and solenoid 62. These components are connected to the other PCB 52 and together form a breath alcohol analyser of the type known per se in the art. Again the breath tube 54 is disposable item kept in a sterile pack.

In use a police officer or other authorised person can conduct a comprehensive test in situ, e.g. at the roadside, on an individual for impairment either through alcohol intoxication or through the influence of drugs such as cannabis or cocaine. The convenient hand-held unit obviates the need to carry separate devices. It will be seen from FIG. 5b that in this embodiment the device is configured so that the disposable peripherals: the breath tube 54 and the electrode module 12 can be fitted simultaneously. The breath test could, for example therefore, be conducted whilst awaiting the results of the drug saliva test.

Figure 6:
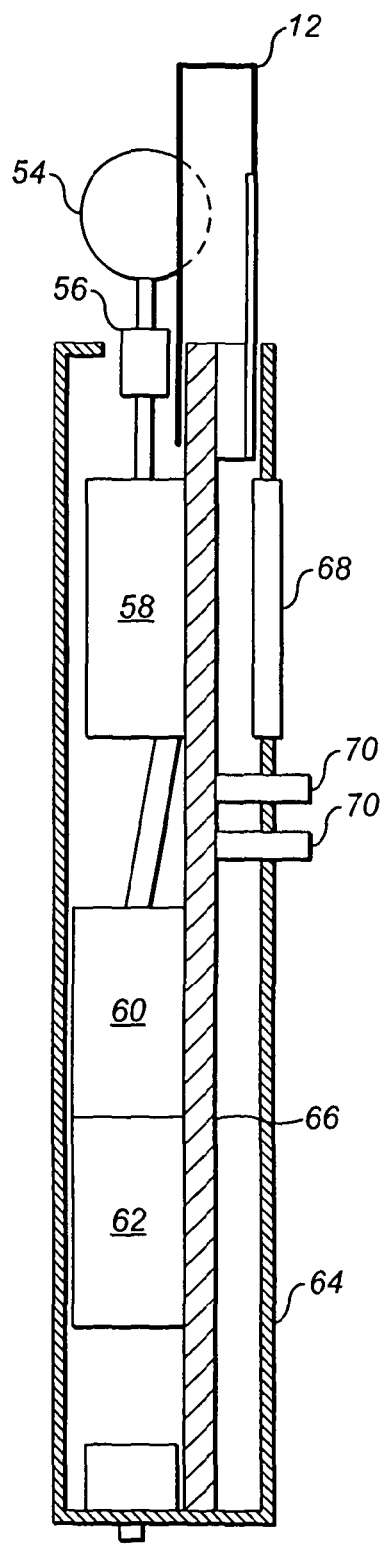
FIG. 6 shows a device according to a further embodiment of the invention.

FIG. 6 shows a side cross-section of another embodiment of the invention. Here the housing 64 contains a single integrated PCB 66 to which are connected a single LCD 68, common operating buttons 70 as well as the electrode module 12 for the saliva test, the fuel cell 58, pump 60 and solenoid 62 for the breath test.

In this embodiment the device is configured so that only one of the electrode module 12 and the breath tube 54 can be fitted at any one time but can sense which peripheral is fitted at any one time and so activate only the corresponding assay.

It will be appreciated that this embodiment is significantly more compact than the previous one and more cost-effective as fewer electronic components are required.

It will also be appreciated by those skilled in the art that only a small number of possible embodiments have been described and that many variations and modifications are possible within the scope of the invention. For example any of the features shown can be used with any other embodiment (whether or not described herein). Although testing of oral fluid for THC is used as an exemplary application of the principles of the invention this is not essential and there are many other possible assays that can be carried out either on oral fluid or on other types of fluid sample.

The invention claimed is:

1. A device for performing at least two assays on separate body fluids comprising an arrangement for carrying out a first electrochemical assay for a first analyte in a sample of breath and an arrangement for carrying out a second electrochemical assay for a second analyte in a sample of liquid, wherein the arrangement for carrying out the second electrochemical assay comprises a swab having an absorbent portion for receiving and retaining a fluid sample, an electrode module comprising at least one electrode, said electrode module being arranged such that it can be selectively placed over said absorbent portion in order to contact said electrode with said fluid sample, the device comprising a reader module configured to process signals from said electrode module.

2. A device as claimed in claim 1 wherein the first analyte is ethanol.

3. A device as claimed in claim 1 wherein the second electrochemical assay is adapted for use with human saliva samples.

4. A device as claimed in claim 1 wherein the arrangement for carrying out the first electrochemical assay and the arrangement for carrying out the second electrochemical assay use a common power supply and/or a common user control interface and/or a common display.

5. A device as claimed in claim 1 wherein the arrangement for carrying out the second electrochemical assay comprises electrodes adapted to detect one of more of: phenols, phenolic compounds and phenol derivatives.

6. A device as claimed in claim 1 wherein said electrode module and said reader module are arranged such that they can be coupled together for communication of said signals from said electrode module to said reader module.

7. A device as claimed in claim 1 wherein the electrode module is removable from the reader module.

8. A device as claimed in claim 1 wherein the electrode module and swab are designed for single use.

9. A device as claimed in claim 1 wherein the electrode module can be locked in place over the absorbent portion of the swab member.

10. A device as claimed claim 1 wherein the electrode module comprises a direct connection to the electrodes, and the reader module comprises a processor for processing or filtering of the signals from the electrodes.

11. A device as claimed in claim 10 wherein the coupling between the electrode module and the reader module comprises a plug-and-socket arrangement.

12. A device as claimed in claim 11 wherein the reader module is configured to identify or verify the electrode module.

13. A device as claimed in claim 11 wherein the reader module is configured to determine automatically what type of electrode module is connected to it, and to perform an appropriate analysis.

14. A device as claimed in claim 1 wherein the electrode module is, or is able to be, rotatably fitted to the swab so as to have an open configuration allowing access to the absorbent portion in order to collect a fluid sample; and a closed configuration in which the absorbent portion is inside the electrode module so that the electrodes thereof can come into contact with the fluid sample.

15. A device as claimed in claim 1 wherein the electrode module can be slid over the absorbent portion of the swab member.

16. A device as claimed in claim 1 wherein the electrode module is permanently fitted to the swab.

17. A device as claimed in claim 1 wherein the electrode module can be fitted over the absorbent portion by a user.

18. A device as claimed in claim 1 wherein the electrode module comprises a working electrode, a counter electrode and a reference electrode.

19. A device as claimed in claim 1 wherein either or both of the electrode module and the swab is configured to apply a contact pressure between said electrodes and the fluid sample retained in the absorbent portion.

20. A device as claimed in claim 19 wherein either or both of the electrode module and the swab comprise a resilient arrangement to apply the contact pressure.

21. A device as claimed in claim 19 wherein the contact pressure is provided by the action of sliding, rotating or otherwise moving the electrode module over the absorbent portion.

22. A device as claimed in claim 19 comprising an arrangement for applying the pressure independently of the action of bringing the electrode module and absorbent portion into registration.

23. A device as claimed in claim 19 wherein the contact pressure is provided by the action of locking the electrode module to the swab.

24. A device as claimed in claim 23 wherein said locking action is coupled to the action of bringing the electrode module into registration with the absorbent portion of the swab.

25. A device as claimed in claim 1 wherein the swab comprises an elongate member with the absorbent portion at one end.

26. A device as claimed in claim 1 wherein the swab comprises an arrangement disposed between the absorbent portion and a handling portion to inhibit fluid running down the swab from the absorbent portion to the handling portion.

27. A device as claimed in claim 1 wherein the swab is sterile for collecting human saliva samples.

28. A device as claimed in claim 1 wherein the electrode module comprises a plurality of working electrodes.

29. A device as claimed in claim 28 comprising a plurality of working electrodes for a single given analyte.

30. A device as claimed in claim 28 wherein two or more working electrodes share a common reference or counter electrode.

31. A device as claimed in claim 28 wherein the plurality of working electrodes is arranged around a common reference or counter electrode.

32. A device as claimed in claim 28 wherein the electrode module comprises between 2 and 30 working electrodes, preferably between 5 and 20 working electrodes, more preferably between 8 and 16 working electrodes.

33. A device as claimed in claim 28 wherein the working electrodes are each less than 2 mm wide, preferably less than 1 mm wide.

34. A device as claimed in claim 28 wherein the plurality of working electrodes are connected together on the electrode module so as to act effectively as a single distributed electrode.

35. A device as claimed in claim 28 wherein the plurality of working electrodes have individual contacts to allow electrical connection to be made to them individually.

36. A device as claimed claim 28 wherein the contacts for the electrodes are provided along one edge of the electrode module.

37. A device for performing at least two assays on separate body fluids comprising an arrangement for carrying out a first electrochemical assay for a first analyte in a sample of breath and an arrangement for carrying out a second electrochemical assay for a second analyte in a sample of liquid, wherein the first electrochemical assay comprises a fuel cell ethanol assay.

* * * * *